United States Patent [19]

Pohl et al.

[11] Patent Number: 4,707,295
[45] Date of Patent: Nov. 17, 1987

[54] BICYCLOOCTANE DERIVATIVES

[75] Inventors: Ludwig Pohl, Darmstadt; Bernhard Scheuble, Alsbach; Andreas Wächtler, Griesheim; Reinhard Hittich, Modautal; Peter Fuss, Mühltal-Traisa, all of Fed. Rep. of Germany

[73] Assignee: Merck Patent Gesellschaft mit beschrankter Haftung, Darmstadt, Fed. Rep. of Germany

[21] Appl. No.: 843,407

[22] Filed: Mar. 24, 1986

[30] Foreign Application Priority Data

Mar. 22, 1985 [DE] Fed. Rep. of Germany ....... 3510433

[51] Int. Cl.$^4$ ................ C09K 19/30; C07C 13/44; C07C 69/753; C07C 69/13; C07C 121/46; C07C 23/32

[52] U.S. Cl. ................ 252/299.62; 252/299.63; 350/350 R; 558/426; 558/428; 558/429; 560/51; 560/53; 560/59; 560/64; 560/65; 560/102; 560/116; 560/118; 560/141; 560/183; 560/187; 560/188; 560/220; 560/221; 560/255; 560/256; 568/327; 568/374; 568/632; 568/634; 568/659; 568/661; 568/664; 568/665; 570/128; 570/129; 570/130; 570/183; 570/187; 570/188; 585/21; 585/26

[58] Field of Search .............. 252/299.62, 299.63, 252/299.61; 350/350 R; 558/426, 428, 429; 560/51, 53, 59, 64, 65, 102, 116, 118, 141, 183, 187, 188, 220, 221, 255, 256; 568/327, 374, 632, 634, 659, 661, 664, 665; 570/128, 129, 130, 183, 187, 188; 585/21, 26

[56] References Cited

U.S. PATENT DOCUMENTS

| 4,219,256 | 8/1980 | Gray et al. | 252/299.62 |
|---|---|---|---|
| 4,261,652 | 4/1981 | Gray et al. | 252/299.62 |
| 4,330,426 | 5/1982 | Eidenschink et al. | 252/299.63 |
| 4,400,061 | 8/1983 | Carr et al. | 252/299.62 |
| 4,478,740 | 10/1984 | Eidenschink et al. | 252/299.62 |
| 4,482,472 | 11/1984 | Carr et al. | 252/299.62 |
| 4,510,069 | 4/1985 | Eidenschink et al. | 252/299.63 |
| 4,514,317 | 4/1985 | Tuone et al. | 252/299.62 |
| 4,528,114 | 7/1985 | Petrzilka | 252/299.61 |
| 4,544,497 | 10/1985 | Abdullah et al. | 252/299.62 |
| 4,551,264 | 11/1985 | Eidenschink et al. | 252/299.62 |
| 4,564,694 | 1/1986 | Hirai et al. | 252/299.63 |
| 4,565,425 | 1/1986 | Petrzilka et al. | 252/299.63 |
| 4,617,140 | 10/1986 | Eidenschink et al. | 252/299.63 |
| 4,622,164 | 11/1986 | Eidenschink et al. | 252/299.63 |
| 4,659,502 | 4/1987 | Fearon et al. | 252/299.61 |
| 4,663,073 | 5/1987 | Sucrow et al. | 252/299.63 |

FOREIGN PATENT DOCUMENTS

| 3407013 | 9/1985 | Fed. Rep. of Germany | 252/299.63 |
|---|---|---|---|
| 3510434 | 9/1986 | Fed. Rep. of Germany | 252/299.63 |
| WO85/01295 | 3/1985 | PCT Int'l Appl. | 252/299.62 |
| 2092169 | 8/1982 | United Kingdom | 252/299.61 |

OTHER PUBLICATIONS

Demus, D. et al., Flüssige Kristalle in Tabellen II, VEB Deutscher Verlag fur Grundstoffindustrie, Leipzig (1984), pp. 85-86.
Gray, G. W., Mol. Cryst. Liq. Cryst., vol. 63, pp. 3-18 (1981).
Gray, G. W. et al., Mol. Cryst. Liq. Cryst., vol. 75, pp. 95-108 (1981).

Primary Examiner—Teddy S. Gron
Attorney, Agent, or Firm—Millen & White

[57] ABSTRACT

Bicyclooctane derivatives of the formula I $$R^1-A^1-A^2-R^2 \qquad \text{I}$$

wherein

R$^1$ and R$^2$ independently of one another are each an alkyl group which has 1-12 C atoms and in which it is also possible for one or two non-adjacent CH$_2$ groups to be replaced by O atoms and/or CO groups and/or —O13 CO groups and/or —CO—O groups and/or —CH=CH— groups, one of the radicals R$^1$ and R$^2$ being also —A$^3$—R$^3$, A$^1$ is a 1,4-cyclohexylene group which is unsubstituted or substituted in the 1-position and/or 2-position and/or 3-position and/or 4-position by alkyl which has in each case 1-5 C atoms and is unsubstituted or substituted or fluorinated, and in which it is also possible for one or two non-adjacent CH$_2$ groups to be replaced by one or two different groupings from the group —O—, —CO—, —CH=CH—, —S—, —SO— or —SO$_2$—, or is substituted by F, Cl, Br, CN and/or CHO, A$^2$ is a 1,4-bicyclo[2.2.2]octylene group, —A$^3$—R$^3$ is —Cy—R$^3$, —Ph—R$^3$, —Cy—Ph—R$^3$ or —Ph—Cy—R$^3$, Cy is 1,4-cyclohexylene or one of the other groups recited for A$^1$, Ph is 1,4-phenylene which is unsubstituted or substituted by or one two F atoms and/or CH$_3$ groups and R$^3$ is an alkyl group which has 1-12 C atoms and in which it is also possible for one or two non-adjacent CH$_2$ groups to be replaced by O atoms and/or CO groups and/or O—CO groups and/or —CO—O groups and/or —CH=CH— groups are suitable for use as components of liquid-crystal phases for field effect and/or bistability effect displys.

19 Claims, No Drawings

BICYCLOOCTANE DERIVATIVES

This invention relates to new bicyclooctane compounds.

Summary of the Invention

It is an object of this invention to provide new, stable, liquid-crystal or mesogenic compounds which are suitable for use as components of liquid-crystal phases.

Upon further study of the specification and appended claims, further objects and advantages of this invention will become apparent to those skilled in the art.

These objects are achieved by providing new bicyclooctane derivatives of the formula I $$R^1-A^1-A^2-R^2 \qquad I$$

wherein $R^1$ and $R^2$ independently of one another are each an alkyl group which has 1-12 C atoms and in which it is also possible for one or two non-adjacent $CH_2$ groups to be replaced by O atoms and/or CO groups and/or —O—CO— groups and/or —CO—O— groups and/or —CH=CH— groups, one of the radicals $R^1$ and $R^2$ also possibly being —$A^3$—$R^3$;

$A^1$ is a 1,4-cyclohexylene group which is unsubstituted or substituted in the 1-position and/or 2-position and/or 3-position and/or 4-position by F, Cl, Br, CN and/or CHO, or by alkyl which has in each case 1-5 C atoms, which alkyl is unsubstituted or substituted or fluorinated, and in which it is also possible for one or two non-adjacent $CH_2$ groups to be replaced by one or two groupings from the group —O—, —CO—, —CH=CH—, —S—, —SO— or —$SO_2$—;

$A^2$ is a 1,4-bicyclo(2,2,2) octylene group ("BCO");
—$A^3$—$R^3$ is —Cy—$R^3$, —Ph—$R^3$, —Cy—Ph—$R^3$ or —Ph—Cy—$R^3$;

Cy is 1,4-cyclohexylene or one of the other qroups recited for $A^1$;

Ph is 1,4-phenylene which is unsubstituted or substituted by one or two F atoms and/or $CH_3$ groups and $R^3$ is an alkyl group which has 1-12 C atoms and in which it is also possible for one or two non-adjacent $CH_2$ groups to be replaced by O atoms and/or CO groups and/or O—CO groups and/or —CO—O groups and/or —CH=CH— groups.

DETAILED DISCUSSION

Like similar compounds, for example those disclosed in German Offenlegungsschrift No. 2,927,277, these substances can be used as components of liquid-crystal phases, in particular for displays based on the principle of the twisted cell, the guest-host effect, the deformation of aligned phases, the effect of dynamic scattering, the field effect or the bistability effect.

It has been found that the bicyclooctane derivatives of the formula I are excellently suitable for use as components of liquid-crystal phases. In particular, it is possible with their aid to prepare stable, liquid-crystal phases which have relatively high $K_3/K_1$ values, a very low optical anisotropy and a positive or negative dielectric anisotropy and which are particularly suitable for field effect displays and/or bistability effect displays. In field effect displays using mixtures of negative dielectric anisotropy, the phases according to the invention exhibit particularly steep characteristic lines, which make it possible to achieve high multiplex ratios. In field effect displays using mixtures of positive dielectric anisotropy, the addition of compounds according to the invention results in particularly flat characteristic lines, which increases the number of possible gray scales.

In liquid-crystal displays having memory properties dependent on bistability effects, the addition of compounds according to the invention results in an increase in tolerance for the uniformity of the layer thickness of the display in relation to the pitch of the liquid-crystal mixture, which decisively facilitates the mass production of such displays.

In addition, providing the compounds of the formula I considerably broadens, in a very general way, the range of liquid-crystal substances which are suitable from various aspects of performance in use for the preparation of liquid-crystal mixtures.

The compounds of the formula I have a wide range of use. Depending on the choice of the substituents, these compounds can be used as base materials of which liquid-crystal dielectrics are predominantly composed; it is also possible, however, to add compounds of the formula I to liquid-crystal base materials belonging to other classes of compounds, in order to influence the optical anisotropy and/or the $K_3/K_1$ values of such a phase.

In the pure state, the compounds of the formula I are colorless and they form liquid-crystal meso-phases within a temperature range which is advantageously situated for electrooptical use. They are very stable to chemicals, heat and light.

The invention therefore relates to the bicyclooctane derivatives of the formula I and to a process for their preparation which consists in treating with a reducing agent a compound which otherwise corresponds to the formula I, but contains one or more reducible group(s) and/or C-C bond(s) instead of H atoms. The invention also relates to the use of the compounds of the formula I as components of liquid-crystal phases. The invention also relates to liquid-crystal phases containing at least one component of the formula I and to liquid-crystal display elements, in particular electrooptical display elements, containing phases of this type.

In the preceding and following text the radicals $R^1$, $R^2$, $R^3$, $A^1$, $A^2$, $A^3$, Ph and Cy have the meaning indicated unless anything to the contrary is expressly noted.

The radicals $R^1$, $R^2$ and $R^3$ are preferably alkyl having 1-10, in particular 3, 4, 5, 6, 7 or 8, C atoms, and are also alkoxy or alkoxymethyl having in each case up to 10, preferably 2, 3, 4, 5, 6, 7 or 8, C atoms. They are preferably linear, and are therefore preferably propyl, butyl, pentylhexyl, heptyl, octyl and also ethoxy, propoxy, butoxy, pentyloxy, heptyloxy, octyloxy, methoxymethyl, ethoxymethyl, propoxymethyl, butoxymethyl, pentyloxymethyl, hexoxymethyl, heptyloxymethyl and also methyl, ethyl, nonyl, decyl, methoxy, nonyloxy, decyloxy, octyloxymethyl, nonyloxymethyl, other linear oxaalkyl and dioxaalkyl groups, such as 3-oxabutyl (=2-methoxyethyl), 3-oxapentyl or 4-oxapentyl, 3-, 4- or 5-oxahexyl, 3-, 4-, 5- or 6-oxaheptyl, 3-, 4, 5-, 6- or 7-oxaoctyl, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl or 1,3-, 1,4-, 1,5-, 2,4-, 2,5- or 3,5-dioxahexyl.

Compounds of the formula I having branched wing groups $R^1$ and/or $R^2$ and/or $R^3$ are important because of improved solubility in the customary liquid-crystal base materials, but can be of particular importance as chiral doping substances if they are optically active. As a rule, branched groups do not contain more than one chain branching.

Preferred branched radicals $R^1$ and/or $R^2$ and/or $R^3$ are isopropyl, 1-methylpropyl (sec.-butyl) or 2-methylpropyl (isobutyl), 2-methylbutyl, 3-methylbutyl (isopentyl), 2-methylpentyl, 3-methylpentyl, 1-methylhexyl, 2-ethylhexyl, 2-propylpentyl, 1-methylheptyl, isopropoxy, 2methylpropoxy, 2-methylbutoxy, 3-methylbutoxy, 2-methylpentyloxy, 3-methylpentyloxy, 2-ethylhexyloxy, 1-methylhexyloxy, 1-methylheptyloxy, 2-oxa-3-methylbutyl and 3-oxa-4-methylpentyl. Fluorinated alkyl is preferably perfluorinated alkyl. Particularly preferred is trifluoromethyl Among the compounds of the formula I, preferred compounds are those in which at least one of the radicals $R^1$ and/or $R^2$ and/or $R^3$ has one of the preferred meanings indicated.

Accordingly, the compounds of the formula I embrace, in particular, compounds of the partial formulae I1 (having two rings), I2 to I5 (having three rings) and I6 to I9 (having four rings):

| | |
|---|---|
| $R^1$—Cy—BCO—$R^2$ | I1 |
| $R^1$—Cy—BCO—Ph—$R^3$ | I2 |
| $R^1$—Cy—BCO—Cy—$R^3$ | I3 |
| $R^3$—Cy—Cy—BCO—$R^3$ | I4 |
| $R^3$—Ph—Cy—BCO—$R^2$ | I5 |
| $R^1$—Cy—BCO—Ph—Cy—$R^3$ | I6 |
| $R^1$—Cy—BCO—Cy—Ph—$R^3$ | I7 |
| $R^3$—Cy—Ph—Cy—BCO—$R^2$ | I8 |
| $R^3$—Ph—Cy—Cy—BCO—$R^2$ | I9 |

In the partial formulae I1 to I9 above, BCO is a group $A^2$, $R^1$, $R^2$ and $R^3$ independently of one another are each preferably alkyl, alkoxy, alkanoyl or alkanoyloxy which is linear in each case and has 3 to 8 carbon atoms wherein alkyl is intended and 2 to 8 carbon atoms wherein alkoxy or alkoxy methyl is intended. Cy and ph have the meaning indicated above. $A^1$(Cy) is preferably an unsubstituted 1,4-cyclohexylene group or a group selected from the formulae (A) to (E)

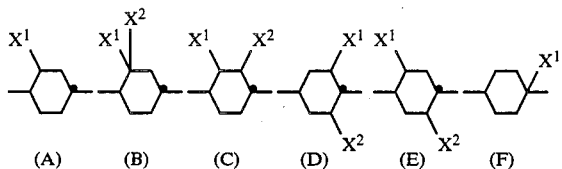

(A)   (B)   (C)   (D)   (E)   (F)

wherein $X^1$ and $X^2$ independently of one another are each preferably F, Cl, CN, $CF_3$, $CH_3$ or $OCH_3$, particularly preferably F or $CH_3$. Of the formulae (A) to (E), (A) is particularly preferred. Formula (F) wherein $X^1$ is CN is also preferred. Above all $A_1$ is preferably an unsubstituted trans-1,4-cyclohexylene group. The group A' also embraces the mirror images of the groups (A) to (E).

Ph is preferably 1,4-phenylene which is unsubstituted or substituted by a fluorine atom.

The substituents of $A^1$ in the 1-position and 4-position are preferably in the trans-configuration.

Compounds of the formulae I1 to I9 wherein, in one of the radicals $R^1$, $R^2$ and $R^3$, a $CH_2$ group has been replaced by a —CH=CH— group, preferably in the ω—, (ω—1)—, (ω—2)—, (ω—3)—, (ω—4)— or (ω—5-)—position, are also preferred.

The compounds of the formula I are prepared by methods which are in themselves known, such as are described in the literature (for example in the standard works, such as Houben-Weyl, Methoden der Organischen Chemie ("Methods of Organic Chemistry"), Georg-Thieme-Verlag, Stuttgart), specifically under reaction conditions which are known and suitable for the reactions mentioned. In this respect it is also possible to make use of variants which are in themselves known, but are not mentioned here in detail.

The starting materials can, if desired, also be formed in situ, in such a way that they are not isolated from the reaction mixture, but are immediately reacted further to give the compounds of the formula I.

Thus the compounds of the formula I can be prepared by reducing a compound which otherwise corresponds to the formula I, but contains one or more reducible groups and/or C-C bonds instead of H atoms.

Suitable reducible groups are preferably carbonyl groups, in particular keto groups, and also, for example, free or esterified hydroxyl groups or halogen atoms attached to aromatic nuclei. Preferred starting materials for the reduction correspond to the formula I, but can contain a cyclohexene ring or cyclohexanone ring instead of a cyclohexane ring, and/or a —CH=CH— group instead of a —$CH_2CH_2$— group, and/or a —CO— group instead of a —$CH_2$— group and/or a free or functionally modified OH group (for example an OH group in the form of its p-toluenesulphonate) instead of an H atom.

The reduction can, for example, be effected by catalytic hydrogenation at temperatures between about 0° and about 200° and pressures between about 1 and 200 bar, in an inert solvent, for example an alcohol, such as methanol, ethanol or isopropanol, an ether such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in aqueous alcoholic solution or in a heterogeneous phase using water/toluene at temperatures between about 80° and 120°) or Wolff-Kishner (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I containing alkyl groups and/or —$CH_2CH_2$— bridges.

Reductions by means of complex hydrides are also possible. For example, arylsulphonyloxy groups can be removed reductively by means of $LiAlH_4$, in particular, p-toluenesulphonyloxymethyl groups can be reduced to methyl groups, preferably in an inert solvent, such as diethyl ether or THF, at temperatures between about 0° and 100°. Double bonds (even in the presence of CN groups!) can be hydrogenated by means of $NaBH_4$ or tributyltin hydride in methanol.

Compounds of the formula I can also be obtained by carrying out an addition reaction between a corresponding cyclohexene derivative (which corresponds to the formula I, but, instead of the radical A, contains a cyclohexene-1,4-diyl group which can carry 1 or 2 further F, Cl or Br atoms and/or CN groups) and a compound of the formula HX (hydrogen fluoride, chloride, bromide or cyanide).

This addition reaction is carried out, for example, in the presence of an inert solvent, for example a halogenated hydrocarbon, such as $CH_2Cl_2$ or $CHCl_3$, a nitrile, such as acetonitrile, or an amide, such as dimethylformamide (DMF) at temperatures between about $-10°$ and $+150°$ and pressures between about 1 and 100 bar. The addition of catalyst can be advantageous, for example an addition reaction with HCN can be catalysed by adding palladium bis-[2,3-0-isopropylidene-2,3-dihydroxy-1,4-bis-(diphenylphosphino)-butane].

Fluorine compounds of the formula I wherein A is a 1,4-cyclohexylene group which is substituted by F and which can additionally carry 1 or 2 further substituents, can be obtained by treating the corresponding hydroxy compounds or bromine or chlorine compounds with a fluorinating agent. The fluorinating agents used can be any compounds which are known for these replacement reactions, for example diethylaminosulphur trifluoride (J. Org. Chem. 40 (5), 574–8 (1975)). The hydroxy, bromine and chlorine compounds can be obtained, for example, from the corresponding cyclohexene compounds by an addition reaction with $H_2O$, HBr or HCl.

In order to prepare compounds of the formula I containing $CF_3$ groups, corresponding carboxylic acids, which, in turn, can be obtained, for example, by the hydrolysis of corresponding nitriles, can be reacted with $SF_4$, preferably with an excess of $SF_4$, under pressure, in the absence or presence of an inert solvent, such as cyclohexane or methylene dichloride, at temperatures between about 70° and 200°. The reaction times range between about 2 hours and about 4 days.

The liquid-crystal phases according to the invention comprise 2 to 20, preferably 3 to 15, components, including at least one compound of the formula I. The other constituents are preferably selected from the nematic or nematogenic substances, in particular the known substances, belonging to the classes of azoxybenzens, benzylideneanilines, biphenyls, terphenyls, phenylbenzoates or cyclohexylbenzoates, phenyl or cyclohexyl cyclohexanecarboxylates, phenylcyclohexane, cyclohexylbiphenyls, cyclohexylcyclohexane, cyclohexylnaphthalenes, 1,4-biscyclohexylbenzenes, 4,4'-biscyclohexylbiphenyls, phenylpyrimidines or cyclohexylpyrimidines, phenylpyridazines or cyclohexylpyridazines and N-oxides thereof, phenyldioxanes or cyclohexyldioxanes, phenyl-1,3-dithianes or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds which are possible as constituents of liquid-crystal phases of this type can be characterized by the formula I'

R'—L—G—E—R"     I' wherein L and E are each a carbocyclic or heterocyclic ring system belonging to the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydro and tetrahydronaphthalene, quinazoline and tetrahydroquinazoline, G is —CH=CH— 

| —CH=CY— | —CH=N(O)— |
|---|---|
| —C≡C— | —CH₂—CH₂— |
| —CO—O— | —CH₂—O— |
| —CO—S— | —CH₂—S— |
| —CH=N— | —COO—Phe—COO— | or a C—C single bond,

Y is halogen, preferably chlorine, or —CN, and

R' and R" are alkyl, alkoxy, alkanoyloxy, alkoxycarbonyl or alkoxycarbonyloxy having up to 18, preferably up to 8 carbon atoms, or one of these radicals is also CN, NC, $NO_2$, $CF_3$, F, Cl or Br.

In most of these compounds R' and R" are different from one another, one of these radicals being in most cases an alkyl or alkoxy group. However, other variants of the substituents envisaged are also customary. Many of such substances or mixtures thereof are commercially available.

All these substances can be obtained by methods known from the literature.

The phases according to the invention contain about 0.1 to 99%, preferably 10 to 95%, of one or more compounds of the formula I. Liquid-crystal phases according to the invention containing 0.1–40%, preferably 0.5–30%, of one or more compounds of the formula I are also preferred.

The preparation of the phases according to the invention is effected in a manner which is in itself customary. As a rule, the components are dissolved in one another, preferably at an elevated temperature.

By means of suitable additives it is possible to modify the liquid-crystal phases according to the invention so that they can be used in all types of liquid-crystal display elements hitherto disclosed.

Additives of this type are known to those skilled in the art and are described in detail in the literature. For example, it is possible to add conductive salts, preferably ethyldimethyldodecylammonium 4-hexyloxybenzoate, tetrabutylammonium tetraphenylboranate or complex salts of crown ethers (cf, for example, I. Haller et al., Mol. Cryst. Liq. Cryst. Volume 24, pages 249–258 (1973)) in order to improve the conductivity, dichroic dyestuffs in order to prepare colored guest-host systems or substances for modifying the dielectric anisotropy, the viscosity and/or the orientation of the nematic phases. Substances of this type are described, for example, in German Offenlegungsschriften Pat. Nos. 2,209,127; 2,240,864; 2,321,632; 2,338,281; 2,450,088; 2,637,430; 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

"Customary working up" means as follows: water is added, the mixture is extracted with methylene chloride, the phases are separated, the organic phase is dried and evaporated and the product is purified by crystallization and/or chromatography.

EXAMPLE 1

A mixture of 3.2 g of 1-n-pentyl-4-(trans-4-propionylcyclohexyl)-bicyclo[2.2.2]octane [obtainable by reacting 1-n-pentyl-4-(trans-4-cyanocyclohexyl)-bicyclo[2.2.2]octane (German Offenlegungsschrift Pat. No. 3,246,440) with $C_2H_5MgBr$ and hydrolysing the product], 3 g of KOH, 5 ml of 85% hydrazine and 50 ml of triethylene glycol is heated at 120° C. for 1 hour. The temperature is increased slowly until the resulting hydrazone is decomposed, and the mixture is boiled for a further 4 hours, cooled and worked up in the customary manner to give 1-n-pentyl-4-(trans-4-n-propylcyclohexyl)-bicyclo[2.2.2]octane.

The following are prepared analogously:

1-Pentyl-4-(trans-4-ethylcyclohexyl)-bicyclo[2.2.2]octane
1-Pentyl-4-(trans-4-butylcyclohexyl)-bicyclo[2.2.2]octane
1-Pentyl-4-(trans-4-pentylcyclohexyl)-bicyclo[2.2.2]octane
1-Pentyl-4-(trans-4-heptylcyclohexyl)-bicyclo[2.2.2]octane
1-Heptyl-4-(trans-4-ethylcyclohexyl)-bicyclo[2.2.2]octane
1-Heptyl-4-(trans-4-propylcyclohexyl)-bicyclo[2.2.2]octane
1-Heptyl-4-(trans-4-butylcyclohexyl)-bicyclo[2.2.2]octane
1-Heptyl-4-(trans-4-pentylcyclohexyl)-bicyclo[2.2.2]octane
1-Heptyl-4-(trans-4-heptylcyclohexyl)-bicyclo[2.2.2]octane
1-Butyl-4-(trans-4-ethylcyclohexyl)-bicyclo[2.2.2]octane
1-Butyl-4-(trans-4-propylcyclohexyl)-bicyclo[2.2.2]octane
1-Butyl-4-(trans-4-butylcyclohexyl)-bicyclo[2.2.2]octane
1-Butyl-4-(trans-4-pentylcyclohexyl)-bicyclo[2.2.2]octane
1-Butyl-4-(trans-4-heptylcyclohexyl)-bicyclo[2.2.2]octane
1-Propyl-4-(trans-4-ethylcyclohexyl)-bicyclo[2.2.2]octane
1-Propyl-4-(trans-4-propylcyclohexyl)-bicyclo[2.2.2]octane
1-Propyl-4-(trans-4-butylcyclohexyl)-bicyclo[2.2.2]octane
1-Propyl-4-(trans-4-pentylcyclohexyl)-bicyclo[2.2.2]octane
1-Propyl-4-(trans-4-heptylcyclohexyl)-bicyclo[2.2.2]octane

EXAMPLE 2

3.1 g of trans-4-(4-n-pentylbicyclo[2.2.2]octan-1-yl)cyclohexanecarboxylic acid is boiled for 1 hour with 2.5 g of $SOCl_2$, and the mixture is evaporated, the resulting crude acid chloride is dissolved in 25 ml of toluene, 1 ml of pyridine and 0.7 g of n-propanol are added, and the mixture is boiled for 2 hours. Cooling and working up in the customary manner gives n-propyl trans-4-(4-n-pentylbicyclo[2.2.2]octan-1-yl)-cyclohexanecarboxylate.

The following are prepared analogously:
Ethyl trans-4-(4-pentylbicyclo[2.2.2]octan-1-yl)cyclohexanecarbosylate
Butyl trans-4-(4-pentylbicyclo[2.2.2]octan-1-yl)cyclohexanecarboxylate
Pentyl trans-4-(4-pentylbicyclo[2.2.2]octan-1-yl)cyclohexanecarboxylate
Ethyl trans-4-(4-heptylbicyclo[2.2.2]octan-1-yl)cyclohexanecarboxylate
Propyl trans-4-(4-heptylbicyclo[2.2.2]octan-1-yl)cyclohexanecarboxylate
Butyl trans-4-(4-heptylbicyclo[2.2.2]octan-1-yl)cyclohexanecarboxylate
Pentyl trans-4-(4-heptylbicyclo[2.2.2]octan-1-yl)cyclohexanecarboxylate
Heptyl trans-4-(4-heptylbicyclo[2.2.2]octan-1-yl)cyclohexanecarboxylate
Ethyl trans-4-(4-butylbicyclo[2.2.2]octan-1-yl)cyclohexanecarboxylate
Propyl trans-4-(4-butylbicyclo[2.2.2]octan-1-yl)cyclohexanecarboxylate
Butyl trans-4-(4-butylbicyclo[2.2.2]octan-1-yl)cyclohexanecarboxylate
Pentyl trans-4-(4-butylbicyclo[2.2.2]octan-1-yl)cyclohexanecarboxylate
Heptyl trans-4-(4-butylbicyclo[2.2.2]octan-1-yl)cyclohexanecarboxylate
Ethyl trans-4-(4-propylbicyclo[2.2.2]octan-1-yl)cyclohexanecarboxylate
Propyl trans-4-(4-propylbicyclo[2.2.2]octan-1-yl)cyclohexanecarboxylate
Butyl trans-4-(4-propylbicyclo[2.2.2]octan-1-yl)cyclohexanecarboxylate
Pentyl trans-4-(4-propylbicyclo[2.2.2]octan-1-yl)cyclohexanecarboxylate
Heptyl trans-4-(4-propylbicyclo[2.2.2]octan-1-yl)cyclohexanecarboxylate

EXAMPLE 3

1-(trans-4-n-Butylcyclohexyl)-4-butyryloxybicyclo[2.2.2]octane is obtained analogously to Example 2 from 8.8 g of butyric acid and 27.8 g of 1-(trans-4-n-butylcyclohexyl)bicyclo[2.2.2]octan-4-ol [obtainable by Wolff-Kishner reduction of 1-(trans-4-n-butylcyclohexyl)-4-hydroxybicyclo[2.2.2]octan-2-one, which, in turn, is obtainable by reacting 4-acetyl-4-(trans-4-n-butylcyclohexyl)-cyclohexanone with trimethyl orthoformate in MeOH/HCl (cf. British Pat. No. 2,065,104; J. Am. Chem. Soc. 86, 5183 (1964); J. Org. Chem. 35, 917 (1970)) and subsequent ether cleavage].

The following are prepared analogously:
1-(trans-4-Ethylcyclohexyl)-4-butyryloxybicyclo[2.2.2]octane octane
1-(trans-4-Propylcyclohexyl)-4-butyryloxybicyclo[2.2.2]octane
1-(trans-4-Pentylcyclohexyl)-4-butyryloxybicyclo[2.2.2]octane
1-(trans-4-Heptylcyclohexyl)-4-butyryloxybicyclo[2.2.2]octane
1-(trans-4-Ethylcyclohexyl)-4-acetoxybicyclo[2.2.2]octane
1-(trans-4-Propylcyclohexyl)-4-acetoxybicyclo[2.2.2]octane
1-(trans-4-Butylcyclohexyl)-4-acetoxybicyclo[2.2.2]octane
1-(trans-4-Pentylcyclohexyl)-4-acetoxybicyclo[2.2.2]octane
1-(trans-4-Heptylcyclohexyl)-4-acetoxybicyclo[2.2.2]octane
1-(trans-4-Ethylcyclohexyl)-4-propionyloxybicyclo[2.2.2]octane 1-(trans-4-Propylcyclohexyl)-4-propionyloxybicyclo[2.2.2]octane
1-(trans-4-Butylcyclohexyl)-4-propionyloxybicyclo[2.2.2]octane
1-(trans-4-Pentylcyclohexyl)-4-propionyloxybicyclo[2.2.2]octane
1-(trans-4-Heptylcyclohexyl)-4-propionyloxybicyclo[2.2.2]octane

EXAMPLE 4

A mixture of 33 g of 2-n-pentyl-5-(4-n-propylbicyclo[2.2.2]octyl)-cyclohexanone [obtainable by the method of P. Place et al., Tetrahedron 34, 1931 (1978) by reacting 3-acetylbutyrolactone with n-pentyl halide/NaH, subsequently reacting the product with hydrogen bromide to give 3-acetyl-1-bromo-n-octane, converting the latter into the corresponding ethylene ketal, reacting the corresponding Grignard compound with 4-cyano-1-n-propylbicyclo[2.2.2]octane and subsequently subjecting the product to an aldol condensation and catalytically hydrogenating the cyclohex-2-enone to give the target product], 20 ml of 80% hydrazine hydrate and 20 g of KOH in 240 ml of diethylene glycol is boiled under reflux for 2 hours. The reflux condenser is then replaced by a distillation column, the temperature is increased slowly to 200° C. and the mixture is kept at this temperature for 6 hours. After cooling, it is diluted with 300 ml of water, acidified and extracted with toluene. Customary working up of the organic phase gives 1-n-propyl-4-(trans-4-n-pentylcyclohexyl)-bicyclo[2.2.2]octane.

The following are obtained analogously by reacting a 4-cyano-1-(trans-4-alkylcyclohexyl)-bicyclo[2.2.2]octane, 4-cyano-1-p-alkylphenylbicyclo[2.2.2]octane, 4-cyano-1-p-(trans-4-alkylcyclohexyl)-phenylbicyclo[2.2.2]octane or 1-alkyl-4-(trans-4-cyanocyclohexyl)-bicyclo[2.2.2]octane with the corresponding Grignard compound from Example 4:

1-(trans-4-Pentylcyclohexyl)-4-(p-ethylphenyl)-bicyclo[2.2.2]octane
1-(trans-4-Pentylcyclohexyl)-4-(p-propylphenyl)-bicyclo[2.2.2]octane
1-(trans-4-Pentylcyclohexyl)-4-(p-butylphenyl)-bicyclo[2.2.2]octane
1-(trans-4-Pentylcyclohexyl)-4-(p-pentylphenyl)-bicyclo[2.2.2]octane
1-(trans-4-Butylcyclohexyl)-4-(p-ethylphenyl)-bicyclo[2.2.2]octane
1-(trans-4-Butylcyclohexyl)-4-(p-propylphenyl)-bicyclo[2.2.2]octane
1-(trans-4-Butylcyclohexyl)-4-(p-butylphenyl)-bicyclo[2.2.2]octane
1-(trans-4-Butylcyclohexyl)-4-(p-pentylphenyl)-bicyclo[2.2.2]octane
1-(trans-4-Propylcyclohexyl)-4-(p-ethylphenyl)-bicyclo2.2.2]octane
1-(trans-4-Propylcyclohexyl)-4-(p-propylphenyl)-bicyclo2.2.2]octane
1-(trans-4-Propylcyclohexyl)-4-(p-butylphenyl)-bicyclo2.2.2]octane
1-(trans-4-Propylcyclohexyl)-4-(p-pentylphenyl)-bicyclo2.2.2]octane
1-(trans-4-Pentylcyclohexyl)4-[p-(trans-4-ethylcyclohexyl)-phenyl]-bicyclo-[2.2.2]octane
1-(trans-4-Pentylcyclohexyl)4-[p-(trans-4-propylcyclohexyl)-phenyl]-bicyclo[2.2.2]octane
1-(trans-4-Pentylcyclohexyl)4-[p-(trans-4-butycyclohexyl)-phenyl]-bicyclo[2.2.2]octane
1-(trans-4-Pentylcyclohexyl)4-[p-(trans-4-butylcyclohexyl)-phenyl]-bicyclo[2.2.2]octane
1-(trans-4-Pentylcyclohexyl)4-[p-(trans-4-pentylcyclohexyl)-phenyl]-bicyclo[2.2.2]octane
1-(trans-4-Butylcyclohexyl)-4-[p-(trans-4-ethylcyclohexyl)-phenyl]-bicyclo[2.2.2]octane
1-(trans-4-Butylcyclohexyl)-4-[p-(trans-4-propylcyclohexyl)-phenyl]-bicyclo[2.2.2]octane
1-(trans-4-Butylcyclohexyl)-4-[p-(trans-4-butylcyclohexyl)-phenyl]-bicyclo[2.2.2]octane
1-(trans-4-Butylcyclohexyl)-4-[p-(trans-4-pentylcyclohexyl)-phenyl]-bicyclo[2.2.2]octane
1-(trans-4-Propylcyclohexyl)-4-[p-(trans-4-ethylcyclohexyl)-phenyl]-bicyclo[2.2.2]octane
1-(trans-4-Propylcyclohexyl)-4-[p-(trans-4-propylcyclohexyl)-phenyl]-bicyclo[2.2.2]octane
1-(trans-4-Propylcyclohexyl)-4-[p-(trans-4-butylcyclohexyl)-phenyl]-bicyclo[2.2.2]octane
1-(trans-4-Propylcyclohexyl)-4-[p-(trans-4-pentylcyclohexyl)-phenyl]-bicyclo[2.2.2]octane
1-(trans-4-Pentylcyclohexyl)-4-(trans-4-ethylcyclohexyl)bicyclo[2.2.2]octane
1-(trans-4-Pentylcyclohexyl)-4-(trans-4-propylcyclohexyl)bicyclo[2.2.2]octane
1-(trans-4-Pentylcyclohexyl)-4-(trans-4-butylcyclohexyl)bicyclo[2.2.2]octane
1-(trans-4-Pentylcyclohexyl)-4-(trans-4-pentylcyclohexyl)bicyclo[2.2.2]octane
1-(trans-4-Butylcyclohexyl)-4-(trans-4-ethylcyclohexyl)bicyclo[2.2.2.]octane
1-(trans-4-Butylcyclohexyl)-4-(trans-4-propylcyclohexyl)bicyclo[2.2.2]octane
1-(trans-4-Butylcyclohexyl)-4-(trans-4-butylcyclohexyl)bicyclo[2.2.2]octane
1-(trans-4-Butylcyclohexyl)-4-(trans-4-pentylcyclohexyl)bicyclo[2.2.2]octane
1-(trans-4-Propylcyclohexyl)-4-(trans-4-ethylcyclohexyl)bicyclo[2.2.2]octane
1-(trans-4-Propylcyclohexyl)-4-(trans-4-propylcyclohexyl)bicyclo[2.2.2]octane
1-(trans-4-Propylcyclohexyl)-4-(trans-4-butylcyclohexyl)bicyclo[2.2.2]octane
1-(trans-4-Propylcyclohexyl)-4-(trans-4-pentylcyclohexyl)bicyclo[2.2.2]octane
1-(trans-4-Ethylcyclohexyl)-4-(trans-4-ethylcyclohexyl)bicyclo[2.2.2]octane
1-(trans-4-Ethylcyclohexyl)-4-(trans-4-propylcyclohexyl)bicyclo[2.2.2]octane
1-(trans-4-Ethylcyclohexyl)-4-(trans-4-butylcyclohexyl)bicyclo[2.2.2]octane
1-(trans-4-Ethylcyclohexyl)-4-(trans-4-pentylcyclohexyl)bicyclo[2.2.2]octane
1-Propyl-4-[trans-4-(trans-4-ethylcyclohexyl)-cyclohexyl]bicyclo[2.2.2]octane
1-Propyl-4-[trans-4-(trans-4-propylcyclohexyl)-cyclohexyl]bicyclo[2.2.2]octane
1-Propyl-4-[trans-4-(trans-4-butylcyclohexyl)-cyclohexyl]bicyclo[2.2.2]octane
1-Propyl-4-[trans-4-(trans-4-pentylcyclohexyl)-cyclohexyl]-bicyclo[2.2.2]octane
1-Butyl-4-[trans-4-(trans-4-ethylcyclohexyl)-cyclohexyl]-bicyclo[2.2.2]octane
1-Butyl-4-[trans-4-(trans-4-propylcyclohexyl)-cyclohexyl ]-bicyclo[2.2.2]octane
1-Butyl-4-[trans-4-(trans-4-butylcyclohexyl)-cyclohexyl]-bicyclo[2.2.2]octane
1-Butyl-4-[trans-4-(trans-4-pentylcyclohexyl)-cyclohexyl]-bicyclo[2.2.2]octane 1-Pentyl-4-[trans-4-(trans-4-ethylcyclohexyl)-cyclohexyl]-bicyclo[2.2.2]octane
1-Pentyl-4-[trans-4-(trans-4-propylcyclohexyl)-cyclohexyl]-bicyclo[2.2.2]octane
1-Pentyl-4-[trans-4-(trans-4-butylcyclohexyl)-cyclohexyl]-bicyclo[2.2.2]octane
1-Pentyl-4-[trans-4-(trans-4-pentylcyclohexyl)-cyclohexyl]-bicyclo[2.2.2]octane
1-Hexyl-4-[trans-4-(trans-4-ethylcyclphexyl)-cyclohexyl]-bicyclo[2.2.2]octane
1-Hexyl-4-[trans-4-(trans-4-propylcyclohexyl)-cyclohexyl]-bicyclo[2.2.2]octane
1-Hexyl-4-[trans-4-(trans-4-butylcyclohexyl)-cyclohexyl]-bicyclo[2.2.2]octane
1-Hexyl-4-[trans-4-(trans-4-pentylcyclohexyl)-cyclohexyl]-bicyclo[2.2.2]octane
1-Heptyl-4-[trans-4-(trans-4-ethylcyclohexyl)-cyclohexyl]-bicyclo[2.2.2]octane
1-Heptyl-4-[trans-4-(trans-4-propylcyclohexyl)-cyclohexyl]-bicyclo[2.2.2]octane
1-Heptyl-4-[trans-4-(trans-4-butylcyclohexyl)-cyclohexyl]-bicyclo[2.2.2]octane
1-Heptyl-4-[trans-4-(trans-4-pentylcyclohexyl)-cyclohexyl]-bicyclo[2.2.2]octane
1-Propyl-4-[trans-4-(p-ethylphenyl)-cyclohexyl]bicyclo[2.2.2]octane
1-Propyl-4-[trans-4-(p-propylphenyl)-cyclohexyl]bicyclo[2.2.2]octane
1-Propyl-4-[trans-4-(p-butylphenyl)-cyclohexyl]bicyclo[2.2.2]octane
1-Propyl-4-[trans-4-(p-pentylphenyl)-cyclohexyl]bicyclo[2.2.2]octane
1-Butyl-4-[trans-4-(p-ethylphenyl)-cyclohexyl]bicyclo[2.2.2]octane
1-Butyl-4-[trans-4-(p-propylphenyl)-cyclohexyl]bicyclo[2.2.2]octane
1-Butyl-4-[trans-4-(p-butylphenyl)-cyclohexyl]bicyclo[2.2.2]octane
1-Butyl-4-[trans-4-(p-pentylphenyl)-cyclohexyl]bicyclo[2.2.2]octane
1-Pentyl-4-[trans-4-(p-ethylphenyl)-cyclohexyl]bicyclo[2.2.2]octane
1-Pentyl-4-[trans-4-(p-propylphenyl)-cyclohexyl]bicyclo[2.2.2]octane
1-Pentyl-4-[trans-4-(p-butylphenyl)-cyclohexyl]bicyclo[2.2.2]octane
1-Pentyl-4-[trans-4-(p-pentylphenyl)-cyclohexyl]bicyclo[2.2.2]octane

EXAMPLE 5

62.5 ml of butyllithium in hexane (1.6 M) and 29.8 g of 1-n-pentyl-4-(trans-4-cyanocyclohexyl)-bicyclo[2.2.2]octane dissolved in 50 ml of toluene are added successively, at $-10°$ and under an atmosphere of nitrogen, to a solution of 10.1 g of diisopropylamine in 70 ml of THF, and the mixture is stirred for 20 minutes. 14.2 g of methyl iodide are then added at $-10°$, and the mixture is stirred for a further 20 minutes at room temperature. Customary working up gives r-1-cyano-1-methyl-cis-4-(4-n-pentylbicyclo[2.2.2]octyl)-cyclohexane and r-1-cyano-1-methyltrans-4-(4-n-pentylbicyclo[2.2.2]octyl)-cyclohexane.

The following are prepared analogously:
1-Cyano-1-methyl-4-(4-ethylbicyclo[2.2.2]octyl)-cyclohexane
1-Cyano-1-methyl-4-(4-propylbicyclo[2.2.2]octyl)-cylohexane
1-Cyano-1-methyl-4-(4-butylbicyclo[2.2.2]octyl)-cyclohexane
1-Cyano-1-methyl-4-(4-heptylbicyclo[2.2.2]octyl)-cyclohexane
1-Cyano-1-ethyl-4-(4-ethylbicyclo[2.2.2]octyl)-cyclohexane
1-Cyano-1-ethyl-4-(4-propylbicyclo[2.2.2]octyl)-cyclohexane
1-Cyano-1-ethyl-4-(4-butylbicyclo[2.2.2]octyl)-cyclohexane
1-Cyano-1-ethyl-4-(4-pentylbicyclo[2.2.2]octyl)-cyclohexane
1-Cyano-1-ethyl-4-(4-heptylbicyclo[2.2.2]octyl)-cyclohexane
1-Cyano-1-propyl-4-(4-ethylbicyclo[2.2.2]octyl)-cyclohexane
1-Cyano-1-propyl-4-(4-propylbicyclo[2.2.2]octyl)-cyclohexane
1-Cyano-1-propyl-4-(4-butylbicyclo[2.2.2]octyl)-cyclohexane
1-Cyano-1-propyl-4-(4-pentylbicyclo[2.2.2]octyl)-cyclohexane
1-Cyano-1-propyl-4-(4-heptylbicyclo[2.2.2]octyl)-cyclohexane
1-Cyano-1-butyl-4-(4-ethylbicyclo[2.2.2]octyl)-cyclohexane
1-Cyano-1-butyl-4-(4-propylbicyclo[2.2.2]octyl)-cyclohexane
1-Cyano-1-butyl-4-(4-butylbicyclo[2.2.2]octyl)-cyclohexane
1-Cyano-1-butyl-4-(4-pentylbicyclo[2.2.2]octyl)-cyclohexane
1-Cyano-1-butyl-4-(4-heptylbicyclo[2.2.2]octyl)-cyclohexane
1-Cyano-1-pentyl-4-(4-ethylbicyclo[2.2.2]octyl)-cyclohexane
1-Cyano-1-pentyl-4-(4-propylbicyclo[2.2.2]octyl)-cyclohexane
1-Cyano-1-pentyl-4-(4-butylbicyclo[2.2.2]octyl)-cyclohexane
1-Cyano-1-pentyl-4-(4-pentylbicyclo[2.2.2]octyl)-cyclohexane
1-Cyano-1-pentyl-4-(4-heptylbicyclo[2.2.2]octyl)-cyclohexane
1-Cyano-1-hexyl-4-(4-ethylbicyclo[2.2.2]octyl)-cyclohexane
1-Cyano-1-hexyl-4-(4-propylbicyclo[2.2.2]octyl)-cyclohexane
1-Cyano-1-hexyl-4-(4-butylbicyclo[2.2.2]octyl)-cyclohexane
1-Cyano-1-hexyl-4-(4-pentylbicyclo[2.2.2]octyl)-cyclohexane
1-Cyano-1-hexyl-4-(4-heptylbicyclo[2.2.2]octyl)-cyclohexane
1-Cyano-1-heptyl-4-(4-ethylbicyclo[2.2.2]octyl)-cyclohexane
1-Cyano-1-heptyl-4-(4-propylbicyclo[2.2.2]octyl)-cyclohexane
1-Cyano-1-heptyl-4-(4-butylbicyclo[2.2.2]octyl)-cyclohexane
1-Cyano-1-heptyl-4-(4-pentylbicyclo[2.2.2]octyl)-cyclohexane
1-Cyano-1-heptyl-4-(4-heptylbicyclo[2.2.2]octyl)-cyclohexane

EXAMPLE 6

A mixture of 29.3 g of 2-n-pentyl-5-(4-n-propylbicyclo[2.2.2]octyl)-cyclohexanone (Example 4) and 13.3 g of diethylaminosulphur trifluoride is warmed slowly to 80° and is stirred for one hour at this temperature. After cooling, the mixture is worked up in the customary manner. This gives 1-n-propyl-4-(trans-4-n-pentyl-3,3-difluorocyclohexyl)-bicyclo[2.2.2]octane.

The following are obtained analogously by reacting corresponding cyclohexanones or cyclohexanols:

1-Ethyl-4-(trans-4-ethyl-3,3-difluorocyclohexyl)-bicyclo-[2.2.2]octane
1-Ethyl-4-(trans-4-propyl-3,3-difluorocyclohexyl)-bicyclo[2.2.2]octane
1-Ethyl-4-(trans-4-butyl-3,3-difluorocyclohexyl)-bicyclo[2.2.2]octane
1-Ethyl-4-(trans-4-pentyl-3,3-difluorocyclohexyl)-bicyclo[2.2.2]octane
1-Butyl-4-(trans-4-ethyl-3,3-difluorocyclohexyl)-bicyclo[2.2.2]octane
1-Butyl-4-(trans-4-propyl-3,3-difluorocyclohexyl)-bicyclo[2.2.2]octane
1-Butyl-4-(trans-4-butyl-3,3-difluorocyclohexyl)-bicyclo[2.2.2]octane
1-Butyl-4-(trans-4-pentyl-3,3-difluorocyclohexyl)-bicyclo[2.2.2]octane
1-Pentyl-4-(trans-4-ethyl-3,3-difluorocyclohexyl)-bicyclo[2.2.2]octane
1-Pentyl-4-(trans-4-propyl-3,3-difluorocyclohexyl)-bicyclo[2.2.2]octane
1-Pentyl-4-(trans-4-butyl-3,3-difluorocyclohexyl)-bicyclo[2.2.2]octane
1-Pentyl-4-(trans-4-pentyl-3,3-difluorocyclohexyl)-bicyclo[2.2.2]octane
1-Propyl-4-(trans-4-ethyl-2-fluorocyclohexyl)-bicyclo-[2.2.2]octane
1-Propyl-4-(trans-4-propyl-2-fluorocyclohexyl)-bicyclo-[2.2.2]octane
1-Propyl-4-(trans-4-butyl-2-fluorocyclohexyl)-bicyclo-[2.2.2]octane
1-Propyl-4-(trans-4-pentyl-2-fluorocyclohexyl)-bicyclo-[2.2.2]octane
1-Butyl-4-(trans-4-ethyl-2-fluorocyclohexyl)-bicyclo-[2.2.2]octane
1-Butyl-4-(trans-4-propyl-2-fluorocyclohexyl)-bicyclo-[2.2.2]octane
1-Butyl-4-(trans-4-butyl-2-fluorocyclohexyl)-bicyclo-[2.2.2]octane
1-Butyl-4-(trans-4-pentyl-2-fluorocyclohexyl)-bicyclo-[2.2.2]octane
1-Pentyl-4-(trans-4-ethyl-2-fluorocyclohexyl)-bicyclo-[2.2.2]octane
1-Pentyl-4-(trans-4-propyl-2-fluorocyclohexyl)-bicyclo-[2.2.2]octane
1-Pentyl-4-(trans-4-butyl-2-fluorocyclohexyl)-bicyclo-[2.2.2]octane
1-Pentyl-4-(trans-4-pentyl-2-fluorocyclohexyl)-bicyclo-[2.2.2]octane
1-Propyl-4-(trans-4-ethyl-3-fluorocyclohexyl)-bicyclo-[2.2.2]octane
1-Propyl-4-(trans-4-propyl-3-fluorocyclohexyl)-bicyclo-[2.2.2]octane
1-Propyl-4-(trans-4-butyl-3-fluorocyclohexyl)-bicyclo-[2.2.2]octane
1-Propyl-4-(trans-4-pentyl-3-fluorocyclohexyl)-bicyclo-[2.2.2]octane The following examples relate to liquid-crystal phases according to the invention:

EXAMPLE A

A liquid-crystal phase consisting of:
24% of p-trans-4-propylcyclohexylbenzonitrile,
20% of p-trans-4-butylcyclohexylbenzonitrile,
29% of p-trans-4-pentylcyclohexylbenzonitrile,
7% of trans-1-p-methoxyphenyl-4-propylcyclohexane,
5% of 1-pentyl-4-(trans-4-propylcyclohexyl)-bicyclo[2.2.2]octane,
4% of 4,4'-bis-(trans-4-propylcyclohexyl)-2-fluorobiphenyl,
4% of 4,4'-bis-(trans-4-pentylcyclohexyl)-2-fluorobiphenyl and
7% of 4-(trans-4-pentylcyclohexyl)-4'-(trans-4-propylcyclohexyl)-2-fluorobiphenyl has a positive dielectric constant anisotropy and a $K_3/K_1$ ratio $> 1.8$.

EXAMPLE B

A liquid-crystal phase consisting of:
24% of p-trans-4-propylcyclohexylbenzonitrile,
20% of p-trans-4-butylcyclohexylbenzonitrile,
29% of p-trans-4-pentylcyclohexylbenzonitrile,
10% of propyl trans-4-(4-pentylbicyclo[2.2.2]octan-1-yl)-cyclohexanecarboxylate
9% of 4-butyl-2-cyanophenyl p-trans-4-propylcyclohexylbenzoate and
8% of 4-cyano-4'-(trans-4-pentylcyclohexyl)-biphenyl has a positive dielectric constant anisotropy and a $K_3/K_1$ ratio $> 1.8$.

EXAMPLE C

A liquid-crystal phase consisting of:
24% of p-trans-4-propylcyclohexylbenzonitrile,
20% of p-trans-4-butylcyclohexylbenzonitrile,
29% of p-trans-4-pentylcyclohexylbenzonitrile,
10% of 4-butyl-2-cyanophenyl p-trans-4-propylcyclohexyl-benzoate,
5% of 1-(trans-4-butylcyclohexyl)-4-butyryloxybicyclo-[2.2.2]octane and
12% of 4-cyano-4'-(trans-4-pentylcyclohexyl)-biphenyl has a positive dielectric constant anisotropy and a $K_3/K_1$ ratio $> 1.9$. This phase is very suitable for field effect displays having a particularly steep characteristic line.

EXAMPLE D

A liquid-crystal phase consisting of:
20% of r-1-cyano-cis-4-(trans-4-propylcyclohexyl)-1-heptylcyclohexane,
17% of r-1-cyano-cis-4-(trans-4-butylcyclohexyl)-1-pentylcyclohexane,
13% of trans-1-p-methoxyphenyl-4-propylcyclohexane,
12% of trans-1-p-ethoxyphenyl-4-propylcyclohexane,
9% of p-propylphenyl p-trans-4-propylcyclohexylbenzoate,
8% of p-propylphenyl p-trans-4-pentylcyclohexylbenzoate,
5% of 4,4'-bis-(trans-4-propylcyclohexyl)-2-fluorobiphenyl,
5% of 4,4'-bis-(trans-4-pentylcyclohexyl)-2-fluorobiphenyl, and
11% of 1-pentyl-4-(trans-4-propylcyclohexyl)-bicyclo[2.2.2]octane has a negative dielectric constant anisotropy and a $K_3/K_1$ ratio $> 1.2$.

EXAMPLE E

A liquid-crystal pha$e consisting of:
15% of r-1-cyano-cis-4-(trans-4-propylcyclohexyl)-1-heptylcyclohexane, 15% of r-1-cyano-cis-4-(trans-4-butylcyclohexyl)-1-pentylcyclohexane,
14% of trans-1-p-methoxyphenyl-4-propylcyclohexane,
12% of trans-1-p-ethoxyphenyl-4-propylcyclohexane,
9% of trans-1-p-butoxyphenyl-4-propylcyclohexane,
5% of 4,4'-bis-(trans-4-propylcyclohexyl)-2-fluorobiphenyl,
5% of 4,4'-bis-(trans-4-pentylcyclohexyl)-2-fluorobiphenyl,
15% of r-1-cyano-1-(p-pentylphenyl)-cis-4-(trans-4-pentylcyclohexyl)-cyclohexane and
10% of propyl trans-4-(4-pentylbicyclo[2.2.2]octan-1-yl)-cyclohexanecarboxylate has a negative dielectric constant anisotropy and a $K_3/K_1$ ratio $>1.3$. This phase is very suitable for field effect displays having a high multiplex ratio.

EXAMPLE F

A liquid-crystal phase consisting of:
15% of r-1-cyano-cis-4-(trans-4-propylcyclohexyl)-1-heptylcyclohexane,
15% of r-1-cyano-cis-4-(trans-4-butylcyclohexyl)-1-pentylcyclohexane,
14% of trans-1-p-methoxyphenyl-4-propylcyclohexane,
12% of trans-1-p-ethoxyphenyl-4-propylcyclohexane,
9% of trans-1-p-butoxyphenyl-4-propylcyclohexane,
5% of 4,4'-bis-(trans-4-propylcyclohexyl)-2-fluorobiphenyl,
5% of 4,4'-bis-(trans-4-pentylcyclohexyl)-2-fluorobiphenyl,
15% of r-1-cyano-1-pentyl-cis-4-[p-(trans-4-pentylcyclohexyl)-phenyl]-cyclohexane and
10% of 1-(trans-4-butylcyclohexyl)-4-butyryloxybicyclo-[2.2.2]octane has a negative dielectric constant anisotropy and a $K_3/K_1$ ratio $>1.3$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase comprising at least two liquid crystalline components, the improvement wherein at least one of said components is a bicyclooctane derivative of the formula $$R^1—A^1—A^2—R^2$$

wherein
R$^1$ and R$^2$ independently are each C$_{1-12}$ alkyl, C$_{1-10}$ alkoxy or C$_{1-12}$ alkyl in which one or two non-adjacent CH$_2$ groups are replaced by CO, —O—CO, —CO—O or —CH=CH—, or one of R$^1$ and R$^2$ can also be —A$^3$—R$^3$,
A$^1$ is a 1,4-cyclohexylene group which is unsubstituted or substituted in the 2—, 3— position or a combination thereof by F, Cl, Br, CN, C$_{1-5}$-alkyl, C$_{1-5}$-alkoxy, or C$_{1-5}$ perfluorinated alkyl,
A$^2$ is a 1,4-bicyclo(2.2.2)octylene group;
A$^3$ is —Cy, —Ph, —Cy—Ph or —Ph—Cy,
Cy is 1,4-cyclohexylene or one of the other groups recited for A$^1$, Ph is 1,4-phenylene which is unsubstituted, or monosubstituted by F, CH$_3$, or a combination thereof,
R$^3$ is C$_{1-12}$ alkyl, C$_{1-10}$ alkoxy or C$_{1-12}$ alkyl wherein one or two non-adjacent CH$_2$ groups are replaced by CO, O—CO, —CO—O, or —CH=CH—.

2. A liquid crystalline phase of claim 1, wherein R$^1$, R$^2$ and R$^3$ are independently C$_{1-10}$-alkyl, or C$_{1-10}$-alkoxy.

3. A liquid crystalline phase of claim 2, wherein R$^1$, R$^2$ and R$^3$ are independently C$_{3-8}$-alkyl, or C$_{2-8}$-alkoxy.

4. A liquid crystalline phase of claim 3, wherein R$^1$, R$^2$ and R$^3$ are independently propyl, butyl, pentyl, hexyl, heptyl, octyl, ethoxy, propoxy, butoxy, pentyloxy, heptyloxy, or octyloxy.

5. A liquid crystalline phase of claim 3, wherein R$^1$, R$^2$ and R$^3$ are independently isopropyl, 1-methylpropyl, 2-methylpropyl, 2-methylbutyl, 3-methylbutyl, 2-methylpentyl, 3-methylpentyl, 1-methylhexyl, 2-ethylhexyl, 2-propylpentyl, 1-methylheptyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy, or 1-methylheptyloxy.

6. A phase of claim 1, wherein the bicyclooctane derivative has the formula $$R^1—Cy—A^2—R^2.$$

7. A phase of claim 1, wherein the bicyclooctane derivative has the formula $$R^1—Cy—A^2—Ph—R^3,$$

$$R^1—Cy—A^2—Cy—R^3,$$

$$R^3—Cy—Cy—A^2—R^3, \text{ or}$$

$$R^3—Ph—Cy—A^2—R^2.$$

8. A phase of claim 1, wherein the bicyclooctane derivative has the formula $$R^1—Cy—A^2—Ph—Cy—R^3,$$

$$R^1—Cy—A^2—Cy—Ph—R^3.$$

$$R^3—Cy—Ph—Cy—A^2—R^2, \text{ or}$$

$$R^3—Ph—Cy—Cy—A^2—R^2.$$

9. A phase of claim 1, wherein A$^1$ is unsubstituted 1,4-cyclohexylene or 1,4-cyclohexylene of the formula

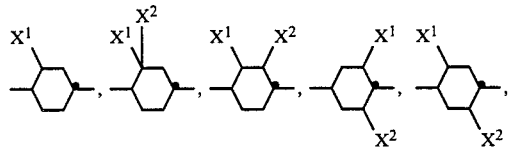

or a mirror image thereof, wherein X$^1$ and X$^2$ independently are F, Cl, CN, CF$_3$, CH$_3$ or OCH$_3$.

10. A liquid crystalline phase of claim 9, wherein X$^1$ and X$^2$ are independently F or CH$^3$.

11. A liquid crystalline phase of claim 10, wherein A$^1$ is

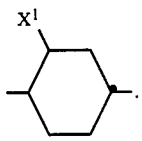

12. A liquid crystalline phase of claim 9, wherein $A^1$ is an unsubstituted trans-1,4-cyclohexylene group.

13. A liquid crystalline phase of claim 1, wherein Ph is 1,4-phenylene or 1,4-phenylene substituted by fluorine.

14. A liquid crystalline phase of claim 9, wherein, in $R^1$, $R^2$ or $R^3$, a $CH_2$ is replaced by —CH=CH— in the $\omega$—, ($\omega$-1)-, ($\omega$-2)-, ($\omega$-3)-, ($\omega$-4)-, or ($\omega$-5)-position.

15. A liquid crystalline phase of claim 1, further comprising at least one nematic or nematogenic compound.

16. A liquid crystalline phase of claim 15, wherein the nematic or nematogenic compound has the formula

R'—L—G—E—R"

wherein

L and E are independently 1,4-disubstituted benzene, 1,4-disubstituted cyclohexane, 4,4'-disubstituted biphenyl, 4,4'-phenylcyclohexane, 4,4'-cyclohexylcyclohexane, 2,5-disubstituted pyrimidine, 1,3-dioxane, 2,6-disubstituted naphthalene, dihydronaphtnalene tetrahydronaphthalene, quinazoline or tetrahydroquinazoline,

| G is | —CH=CH—, | —N(O)—N—, |
|---|---|---|
| | —CH=CY—, | —CH=N(O)—, |
| | —C≡C—, | —CH$_2$—CH$_2$—, |
| | —CO—O—, | —CH$_2$—O—, |
| | —CO—S—, | —CH$_2$—S—, |
| | —CH=N—, | —COO—Phe—COO—, | or a C-C single bond,

Y is chlorine or —CN, and

R' and R" are alkyl, alkoxyl, alkanoyloxy, alkoxycarbonyl or alkoxycarbonyloxy having up to 18 carbon atoms, or one of R' or R" is CN, NC, NO$_2$, CF$_3$, F, Cl or Br.

17. In a display element, based on a liquid crystal phase, the improvement wherein the phase is one of claim 1.

18. In an electrooptical display element based in a liquid crystalline dielectric, the improvement wherein the dielectric is a phase of claim 1.

19. A bicyclooctane derivative of the formula formula $R^1$—$A^1$—$A^2$—$R^2$ wherein $R^1$ and $R^2$ independently are each $C_{1-12}$ alkyl, $C_{1-10}$ alkoxy or $C_{1-12}$ alkyl in which one or two non-adjacent $CH_2$ groups are replaced by CO, or —CH=CH—, or one of $R^1$ and $R^2$ can also be —$A^3$—$R^3$, $A^1$ is a 1,4-cyclohexylene group which is unsubstituted or substituted in the 2-, 3- position or a combination thereof by F, Cl, Br, CN, $C_{1-5}$-alkyl, $C_{1-5}$-alkoxy, or $C_{1-5}$ perflurinated alkyl, $A^2$ is a 1,4-bicyclo(2.2.2)octylene group;

$A^3$ is —Cy, —Ph, —Cy—Ph or —Ph—Cy,

Cy is 1,4-cyclohexylene or one of the other groups recited for $A^1$,

Ph is 1,4-phenylene which is unsubstituted, or monosubstituted by F, CH$_3$, or a combination thereof, $R^3$ is $C_{1-12}$ alkyl, $C_{1-10}$ alkoxy or $C_{1-12}$ alkyl wherein one or two non-adjacent $CH_2$ groups are replaced by CO, O-CO, -CO-O, or -CH=CH-.

* * * * *